(12) United States Patent
Andersen

(10) Patent No.: US 7,481,653 B2
(45) Date of Patent: *Jan. 27, 2009

(54) PRESHAPED THIN-WALLED DENTAL TRAYS AND METHODS OF MANUFACTURING AND USING SUCH TRAYS

(75) Inventor: Scot N. Andersen, Draper, UT (US)

(73) Assignee: OraTech LC, Draper, UT (US)

( * ) Notice: Subject to any disclaimer, the term of this patent is extended or adjusted under 35 U.S.C. 154(b) by 506 days.

This patent is subject to a terminal disclaimer.

(21) Appl. No.: 11/054,696

(22) Filed: Feb. 9, 2005

(65) Prior Publication Data

US 2005/0136381 A1    Jun. 23, 2005

Related U.S. Application Data

(63) Continuation of application No. 10/701,788, filed on Nov. 4, 2003, now Pat. No. 6,964,571, which is a continuation-in-part of application No. 10/350,629, filed on Jan. 24, 2003, now Pat. No. 7,004,756.

(51) Int. Cl.
*A61C 5/00* (2006.01)
(52) U.S. Cl. .......................................... 433/215; 433/37
(58) Field of Classification Search ................. 433/215, 433/37, 49, 53
See application file for complete search history.

(56) References Cited

U.S. PATENT DOCUMENTS

| | | |
|---|---|---|
| 165,584 A | 7/1875 | Hopfen |
| 1,637,153 A | 7/1927 | Lawton |
| 2,257,709 A | 9/1941 | Anderson ................... 128/260 |
| 2,835,628 A | 5/1958 | Saffir ........................... 167/84 |
| 3,339,547 A | 9/1967 | Drabkowski ................ 128/260 |

(Continued)

FOREIGN PATENT DOCUMENTS

WO    WO 88/06869    9/1998

(Continued)

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).

*Primary Examiner*—John J Wilson
(74) *Attorney, Agent, or Firm*—Workman Nydegger

(57) ABSTRACT

Pre-shaped, non-custom dental trays are either preloaded with a dental treatment composition (e.g., in the form of a gel) or filled with a dental treatment composition just prior to placement over a person's teeth. The pre-shaped dental tray is thin and flexible, which allows it to be placed over a person's teeth and then approximately conform to the person's teeth. The pre-shaped, non-custom dental trays can therefore perform similar to a customized tray but without having to go through the more lengthy customization procedure. According to one embodiment, a pre-shaped dental tray can be preloaded with a dental treatment composition and stored within a sealed packaging container. Alternatively, it can be sold by itself or in combination with a treatment composition that a user can load into the dental tray. The tray can be manufactured by vacuum forming polymeric sheet material over a template.

11 Claims, 6 Drawing Sheets

U.S. PATENT DOCUMENTS

| | | | |
|---|---|---|---|
| 3,527,219 A | 9/1970 | Greenberg | 128/260 |
| 3,577,640 A | 5/1971 | Lee | 32/32 |
| 3,624,909 A | 12/1971 | Greenberg | 32/40 |
| 3,688,406 A | 9/1972 | Porter et al. | 32/40 R |
| 3,878,610 A * | 4/1975 | Coscina | 433/37 |
| 3,955,281 A | 5/1976 | Weitzman | 32/14 B |
| 4,044,762 A | 8/1977 | Jacobs | 128/136 |
| 4,063,552 A | 12/1977 | Going et al. | 128/136 |
| 4,064,628 A | 12/1977 | Weitzman | 32/14 B |
| 4,138,814 A | 2/1979 | Weitzman | 32/14 B |
| RE33,093 E | 10/1989 | Schiraldi et al. | 424/676 |
| 4,900,721 A | 2/1990 | Bansemir et al. | 514/25 |
| 4,902,227 A | 2/1990 | Smith | 433/215 |
| 5,008,093 A | 4/1991 | Merianos | 423/272 |
| 5,051,476 A | 9/1991 | Uji et al. | 525/186 |
| 5,085,585 A | 2/1992 | Zimble | 433/80 |
| 5,108,742 A | 4/1992 | Merianos | 424/78.32 |
| 5,112,225 A | 5/1992 | Diesso | 433/48 |
| 5,183,901 A | 2/1993 | Login et al. | 548/543 |
| 5,211,559 A | 5/1993 | Hart et al. | 433/80 |
| 5,310,563 A | 5/1994 | Curtis et al. | 424/616 |
| 5,326,685 A | 7/1994 | Gaglio et al. | 433/215 |
| 5,346,061 A | 9/1994 | Newman et al. | 206/221 |
| 5,356,291 A | 10/1994 | Darnell | 433/216 |
| 5,376,006 A | 12/1994 | Fischer | 433/215 |
| 5,425,953 A | 6/1995 | Sintov et al. | 424/404 |
| 5,562,449 A | 10/1996 | Jacobs et al. | 433/215 |
| 5,573,399 A | 11/1996 | McClintock, II | 433/80 |
| 5,575,654 A | 11/1996 | Fontenot | 433/215 |
| 5,611,687 A | 3/1997 | Wagner | 433/80 |
| 5,616,027 A | 4/1997 | Jacobs et al. | 433/37 |
| 5,631,000 A | 5/1997 | Pellico | 424/53 |
| 5,639,445 A | 6/1997 | Curtis et al. | 424/49 |
| 5,702,251 A | 12/1997 | McClintock, II | 433/80 |
| 5,707,235 A | 1/1998 | Knutson | 433/213 |
| 5,711,935 A | 1/1998 | Hill et al. | 424/49 |
| 5,752,826 A | 5/1998 | Andreiko | 433/41 |
| 5,769,633 A | 6/1998 | Jacobs et al. | 433/37 |
| 5,816,802 A | 10/1998 | Montgomery | 433/80 |
| 5,846,058 A | 12/1998 | Fischer | 433/216 |
| 5,851,512 A | 12/1998 | Fischer | 424/49 |
| 5,863,202 A | 1/1999 | Fontenot et al. | 433/215 |
| 5,879,691 A | 3/1999 | Sagel et al. | 429/401 |
| 5,891,453 A | 4/1999 | Sagel et al. | 424/401 |
| 5,894,017 A | 4/1999 | Sagel et al. | 424/401 |
| 5,895,218 A | 4/1999 | Quinn et al. | 433/80 |
| 5,922,307 A | 7/1999 | Montgomery | 424/53 |
| 5,924,863 A | 7/1999 | Jacobs et al. | 433/80 |
| 5,980,249 A | 11/1999 | Fontenot | 433/80 |
| 5,985,249 A | 11/1999 | Fischer | 424/49 |
| 5,989,569 A | 11/1999 | Dirksing et al. | 424/401 |
| 6,036,943 A | 3/2000 | Fischer | 424/49 |
| 6,045,811 A | 4/2000 | Dirksing et al. | 424/401 |
| 6,080,397 A | 6/2000 | Pfirrmann | 424/78.08 |
| 6,089,869 A | 7/2000 | Schwartz | 433/215 |
| 6,096,328 A | 8/2000 | Sagel et al. | 424/401 |
| 6,106,293 A | 8/2000 | Wiesel | 433/215 |
| 6,126,443 A | 10/2000 | Burgio | 433/215 |
| 6,136,297 A | 10/2000 | Sagel et al. | 424/49 |
| 6,142,780 A | 11/2000 | Burgio | 433/80 |
| 6,155,832 A | 12/2000 | Wiesel | 433/215 |
| 6,183,251 B1 | 2/2001 | Fischer | 433/48 |
| 6,197,331 B1 | 3/2001 | Lerner et al. | 424/448 |
| 6,247,930 B1 | 6/2001 | Chiang et al. | 433/80 |
| 6,274,122 B1 | 8/2001 | McLaughlin | 424/53 |
| 6,277,458 B1 | 8/2001 | Dirksing et al. | 424/42.3 |
| 6,280,196 B1 | 8/2001 | Berghash | 433/215 |
| 6,287,120 B1 | 9/2001 | Wiesel | 433/215 |
| 6,306,370 B1 | 10/2001 | Jensen et al. | 424/49 |
| 6,309,625 B1 | 10/2001 | Jensen et al. | 424/49 |
| 6,312,671 B1 | 11/2001 | Jensen et al. | 424/53 |
| 6,322,360 B1 | 11/2001 | Burgio | 433/80 |
| 6,331,292 B1 | 12/2001 | Montgomery | 424/53 |
| 6,343,932 B1 | 2/2002 | Wiesel | 433/215 |
| 6,649,147 B1 | 2/2002 | Ye et al. | 424/49 |
| 6,682,721 B2 | 2/2002 | Kim et al. | 424/53 |
| 6,364,665 B1 | 4/2002 | Trettemerp | 433/215 |
| 6,379,147 B1 | 4/2002 | Georgakis et al. | 433/37 |
| 6,419,903 B1 | 7/2002 | Xu et al. | 424/49 |
| 6,419,906 B1 | 7/2002 | Xu et al. | 424/53 |
| 6,435,873 B1 | 8/2002 | Burgio | 433/80 |
| 6,440,396 B1 | 8/2002 | McLaughlin | 424/49 |
| 6,689,344 B2 | 9/2002 | Chang et al. | 424/53 |
| 6,458,380 B1 | 10/2002 | Leaderman | 424/443 |
| 6,461,158 B1 | 10/2002 | Sagel et al. | 433/30 |
| 6,730,316 B2 | 11/2002 | Chen | 424/435 |
| 6,488,914 B2 | 12/2002 | Montgomery | 424/53 |
| 6,497,575 B2 | 12/2002 | Zavitsanos et al. | 433/215 |
| 6,500,408 B2 | 12/2002 | Chen | 424/53 |
| 6,503,486 B2 | 1/2003 | Xu et al. | 424/53 |
| 6,506,053 B2 | 1/2003 | Wiesel | 433/215 |
| 6,514,483 B2 | 2/2003 | Xu et al. | 424/53 |
| 6,514,484 B2 | 2/2003 | Rajaiah et al. | 424/53 |
| 6,551,579 B2 | 4/2003 | Sagel et al. | 424/53 |
| 2001/0046654 A1 | 11/2001 | Zavitsanos et al. | 433/32 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0081555 A1 | 6/2002 | Wiesel | 433/215 |
| 2002/0164292 A1 | 11/2002 | Peterson et al. | 424/53 |
| 2002/0182154 A1 | 12/2002 | McLaughlin | 424/53 |
| 2002/0187111 A1 | 12/2002 | Xu et al. | 424/53 |
| 2002/0187112 A1 | 12/2002 | Xu et al. | 424/53 |
| 2003/0003421 A1 | 1/2003 | Besenheider et al. | 433/215 |
| 2003/0012747 A1 | 1/2003 | Peterson | 424/53 |
| 2003/0036037 A1 | 2/2003 | Zavitsanos et al. | 433/215 |
| 2003/0044631 A1 | 3/2003 | Sagal et al. | 428/548 |
| 2003/0068284 A1 | 4/2003 | Sagal et al. | 424/53 |
| 2003/0068601 A1 | 4/2003 | Zavitsanos et al. | 433/215 |
| 2003/0082114 A1 | 5/2003 | Kim et al. | 424/53 |
| 2003/0133884 A1 | 7/2003 | Chang et al. | 424/53 |
| 2003/0194382 A1 | 10/2003 | Chang et al. | 424/53 |
| 2003/0198606 A1 | 10/2003 | Kim et al. | 424/53 |

FOREIGN PATENT DOCUMENTS

| | | |
|---|---|---|
| WO | WO 03/000216 | 1/2003 |

* cited by examiner

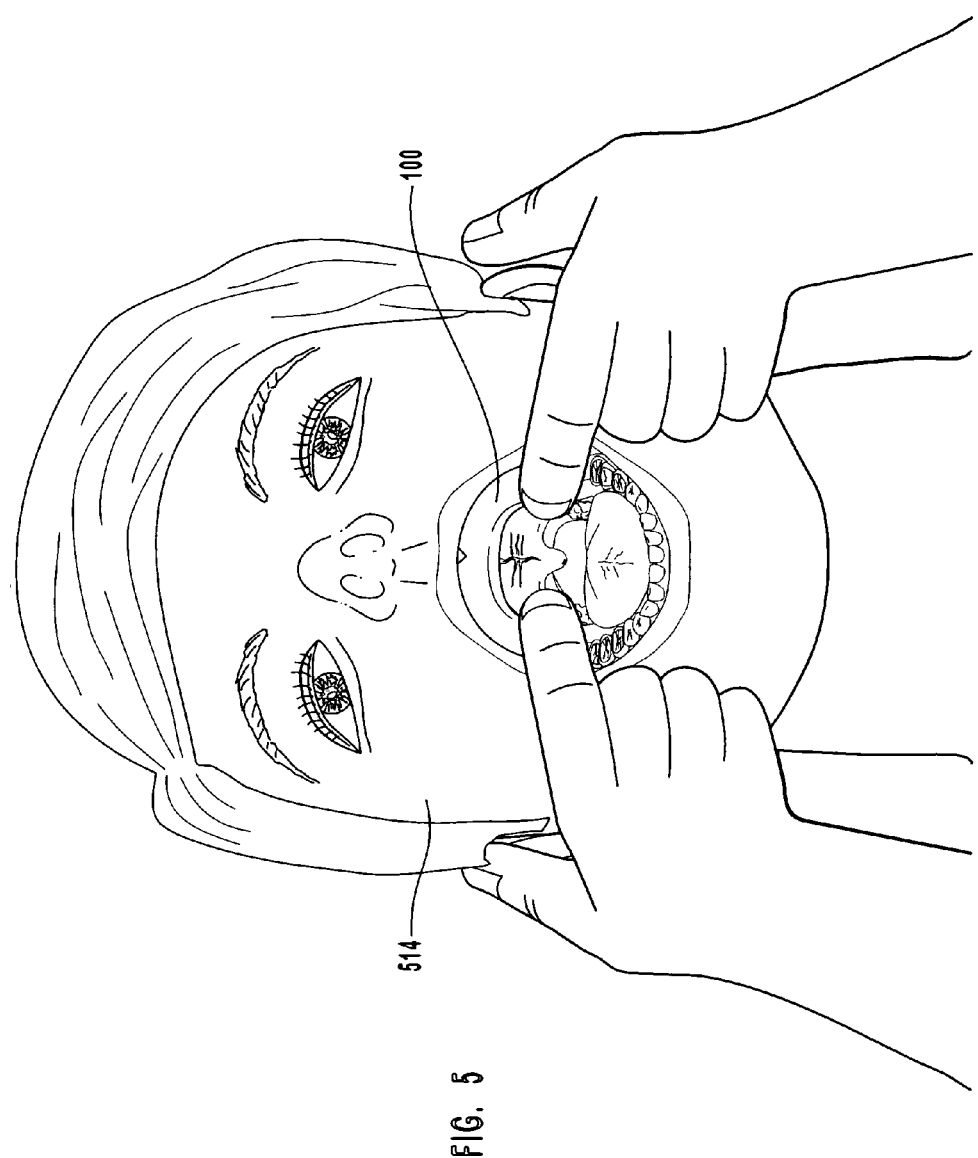

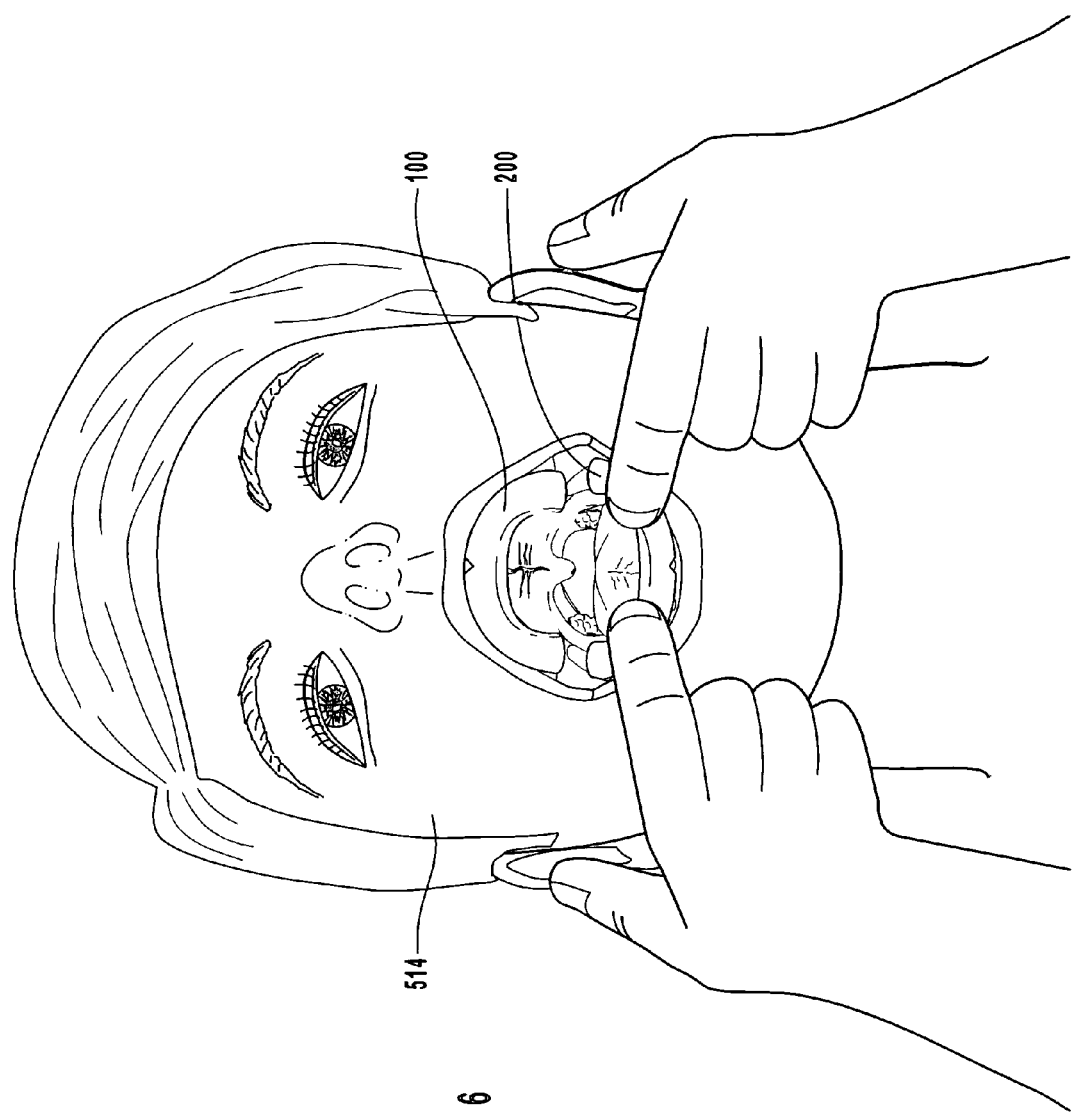

PRESHAPED THIN-WALLED DENTAL TRAYS AND METHODS OF MANUFACTURING AND USING SUCH TRAYS

CROSS-REFERENCE TO RELATED APPLICATIONS

This application is a continuation of U.S. application Ser. No. 10/701,788, filed Nov. 4, 2003, now U.S. Pat. No. 6,964,571 which is a continuation-in-part of U.S. application Ser. No. 10/350,629, filed Jan. 24, 2003. now U.S. Pat. No. 7,004,756. The disclosures of the foregoing applications are incorporated in their entirety.

BACKGROUND OF THE INVENTION

1. The Field of the Invention

The present invention is in the field of dental trays used to provide a desired dental treatment to a person's teeth. More particularly, the invention relates to pre-shaped, non-custom dental trays that are useful in applying a dental treatment composition to a person's teeth (e.g., a dental bleaching composition).

2. The Relevant Technology

Virtually all people desire white or whiter teeth. To achieve this goal, people either a have veneers placed over their teeth or have their teeth chemically bleached. In the past, patients who desired to have their teeth bleached had to submit to conventional in-office bleaching techniques. The process generally involves: (1) making an alginate impression of the patient's teeth; (2) making a stone cast or model of the impression; (3) vacuum forming a dental tray from the model, usually from a heated sheet of thin ethyl vinyl acetate (EVA) material, and (4) trimming to exclude gingival coverage. This method results in a tray that is soft and flexible, that is customized to very accurately fit over the patient's teeth, and that is therefore very comfortable to wear. However, the process for making a customized tray is time consuming, often taking days or weeks before the customized tray is available to the patient, and the resulting tray is quite expensive.

Because of the time and cost associated with customized trays, less costly alternatives have been developed, but these alternatives have substantial disadvantages in terms of accuracy, effectiveness, and comfort.

One alternative is the so-called "boil and bite" tray. A relatively thick, non-custom preformed tray (similar to a mouth guard) made of EVA or polyethylene or other material is submerged in boiling water. The preformed tray is relatively thick (e.g., >2 mm) to prevent the tray from collapsing on itself and becoming entirely unusable during the heating process. Upon removal from the heated water, the tray is quickly placed inside the patient's mouth. The patient quickly bites down and applies contact pressure to make an impression of the biting surfaces of the user's teeth. One problem with "boil and bite" trays is that they are relatively thick and bulky, which make them more intrusive and less comfortable to wear compared to customized trays. The thickness of large, bulky preformed trays also limits the accuracy with which they can conform to the user's teeth and/or gums and makes the trays more rigid.

To the extent that boil and bite trays made from EVA and like materials are made with thinner walls, such trays are extremely difficult to work with because they tend to shrivel and collapse outside extremely narrow windows of temperature and heating time. For example, if left in a hot water bath too long (i.e., for more than a few seconds) they can quickly become limp and lose their pre-form shape, making it difficult or impossible to conform the tray to the user's teeth. In view of the foregoing, "boil and bite" trays that do not have the tendency to collapse and shrivel when heated generally do not accurately conform to the user's teeth and are bulky and uncomfortable to wear.

Another alternative for teeth bleaching involves non-customized strips of a flexible plastic material coated with a bleaching agent that can be applied to the teeth. Such strips are placed against the teeth by the user to cover the labial surface of the front 6 teeth. Such strips do not readily surround the dental arch, and are rather ineffective in holding the bleaching composition against the teeth. Because the structure of the device is a simple strip that is initially flat, they are awkward to place and may not hold the bleaching agent against the teeth long enough for a single treatment to have the desired effect. Frequent replacement and refitting of the strips is often required. In addition, they treat only the teeth at the front of the dental arch, they provide little or no treatment of the lingual surfaces of the tooth, and they do not provide adequate treatment to the margins between the teeth. Finally, the upper and lower dental arches are typically bleached individually. Trying to place separate strips over the upper and lower dental arches at the same time can be quite difficult.

Another alternative is a dual tray assembly as disclosed in U.S. Pat. No. 5,616,027 to Jacobs et al. The dual tray assembly is composed of an outer tray that supports or carries an inner tray made of a thermoplastic material comprising EVA. In use, the tray assembly is submerged in hot water, whereby the inner tray becomes pliable and moldable and the outer tray remains rigid. The heated assembly is then placed in the mouth of the patient where the inner tray takes an impression of the patient's teeth. Thereafter, the assembly is removed from the patient's mouth and the inner tray is removed from the assembly and trimmed so as to yield a customized tray that is thinner and more comfortable to wear compared to conventional "boil and bite" trays.

In view of the foregoing, there is an ongoing need to develop alternatives that are simpler to use but that result in a comfortable-fitting dental tray in order to promote compliance with a particular treatment regimen.

BRIEF SUMMARY OF THE INVENTION

The present invention is directed to pre-shaped, non-custom dental trays that are either preloaded with a dental treatment composition or filled with a dental treatment composition just prior to placement over a person's teeth. The pre-shaped dental trays are thin-walled so that they can be placed over a person's teeth and/or gums and thereafter substantially conform to the person's teeth and/or gums without the need to formally customize the tray. The dental trays may be preloaded with a dental treatment composition so as to yield a dental treatment device that is simple and easy to use.

The tray is preferably available in different configurations for treatment of the upper and lower dental arches. Each tray is configured so as to cover at least a portion of the teeth and/or gums of a dental arch. Differences in the configurations of the upper and lower trays are intended to generally match the differences in a typical upper versus lower dental arch (e.g. the front surfaces of the front teeth of the upper arch are generally taller than the corresponding surfaces of the teeth of the lower arch). The pre-shaped dental trays are sufficiently flexible so that they are able to conform to a wide variety of differently-sized teeth and dental arches.

Each tray includes at least two walls that define a hollow interior portion, or trough. According to one embodiment the tray includes a bottom wall having a generally horseshoe shape, a front side wall extending laterally upward from a front side of the bottom wall, and a rear side wall extending laterally upward from a rear side of the bottom wall. The bottom wall, front side wall, and rear side wall define a hollow interior, or trough, into which a dental treatment composition can be placed. The front and rear side walls may be parallel or flared, the latter providing a larger top opening than the width of the bottom wall.

The dental tray may also include a notch within the front side wall, preferably within an edge near the center of the front side wall, and/or a notch within the rear side wall, preferably within an edge near the center of the rear side wall. Such notches allow the tray to more easily spread open and conform to larger-sized dental arches. In this way, the tray can be "one-size fits all" (or at least most).

The tray is formed of a thermoplastic elastomer, for example, low or ultra low density polyethylene (LDPE or ULDPE), either alone or blended with one or more additional polymers, e.g., ethylene-vinyl acetate copolymer ("EVA"), polycaprolactone ("PCL"), other types of polyethylene ("PE"), polypropylene ("PP"), or other plastic materials. LDPE, ULDPE, PE and PP are examples of polyolefins. Alternatively, the tray may comprise one or more of ethylene vinyl acetate (EVA), polycaprolactone (PCL), or other thermoplastic materials. Plasticizers, flow additives, and fillers known in the art can be used as desired to modify the properties of the material used to form the tray.

According to one embodiment, the tray is formed of a mixture of EVA and PP, comprising about 5 percent to about 35 percent polypropylene (PP), more preferably about 10 percent to about 30 percent polypropylene (PP), and most preferably about 15 percent to about 25 percent polypropylene (PP). The balance comprises ethylene-vinyl acetate (EVA), and optionally small quantities of additives.

The pre-shaped tray is generally thin-walled and flexible, with a wall thickness preferably in a range of about 0.05 mm to about 1 mm, more preferably in a range of about 0.075 mm to about 0.75 mm, and most preferably in a range of about 0.1 mm to about 0.5 mm. The non-custom trays according to the invention are preferably sufficiently flexible so that, when a pre-shaped tray is placed over a person's teeth, the tray will at least partially conform to the person's teeth during use. In this way, the pre-shaped, non-custom trays can approximate the comfort and fit of a customized dental tray.

According to one embodiment, the tray may be configured so as to cover the occlusal, front, and rear surfaces of the teeth of the dental arch. In this way, both the front and rear surface of a person's teeth can be treated simultaneously. Optionally, the tray may be configured to cover portions of the gums for periodontal treatments. In one embodiment, the front side wall of the dental tray may be contoured to approximately correspond to the natural curvature of the labial and buccal surfaces of a person's teeth in order to assist adhesion to teeth, particularly the canines, which are typically more difficult to adhere to.

The tray is designed so that no heating of the tray or customization to the person's teeth is required prior to use. Instead, the pre-shaped tray is designed so as to be used by simply placing a tray loaded with a dental treatment composition over the person's teeth. Two trays can optionally be used to treat the upper and lower dental arches simultaneously or the dental arches may be treated separately or sequentially.

In one embodiment, the dental tray is used with a dental bleaching composition. The bleaching composition preferably has a high enough concentration of bleaching agent to allow for substantially reduced wear time. A typical wear time is 30-60 minutes daily for five consecutive days. The bleaching gel may include polyethylene glycol (PEG) or propylene glycol (PPG), both of which can act either as thickening agents or liquid carriers depending on their molecular weight, glycerin, carbamide peroxide or hydrogen peroxide, and other components. Other thickening agents that may be used include polyvinyl pyrrolidone (PVP), carboxypolymethylene, carboxymethyl cellulose, and the like. PVP and carboxypolymethylene have been found to be especially useful in making treatment compositions that are sticky and viscous.

The treatment compositions may contain other active agents in addition to, or instead of, the dental bleaching agent, e.g., antimicrobial agents (e.g. for a periodontal gum disorder treatment), anticariogenic agents, remineralizing agents, and the like. The treatment compositions may contain a thickening agent in order for the compositions to be sufficiently thick so that, when the non-custom dental tray is placed over a person's teeth, the dental treatment composition will hold the tray against the person's teeth and allow the tray to at least partially conform to the person's teeth.

The trays of the present invention are useful for tooth bleaching or other dental treatments. When the tray is preloaded with a bleaching gel or other dental composition already preloaded in the tray, it can be applied to a person's teeth and/or gums by simply placing the tray over the person's teeth. Pre-loaded trays may be stored within a sealed packaging container to protect the active agents and kept the dental trays clean prior to use. The tray may alternatively not be preloaded with a treatment composition, allowing the user to fill the tray with any desired composition prior to insertion over the person's teeth.

The fact that the pre-shaped, non-custom dental tray does not require heating or customization to the person's teeth makes it less expensive and easier to use compared to boil and bite trays or trays that are customized using a stone model of the person's teeth. The inventive trays can be sold over-the-counter for at-home use, reducing time and cost and eliminating any visits to a dental practitioner. Optionally, the tray may be provided as part of a dental bleaching kit containing one or more trays sized and configured for treatment of both the upper and lower dental arches, together with one or more dental treatment compositions, e.g., a bleaching gel.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 5 illustrates a person placing a dental tray according to the invention over the upper dental arch; and FIG. 6 illustrates a person placing a dental tray according to the invention over the lower dental arch with a preloaded tray already placed over the upper dental arch.

DETAILED DESCRIPTION OF THE PREFERRED EMBODIMENTS

As summarized above, the present invention is directed to pre-shaped, non-custom dental trays that are either preloaded with a dental treatment composition or which can be filled with treatment composition just prior to use. The pre-shaped dental tray is a thin, soft, optionally clear, non-custom tray having sufficient structural integrity so that it can be easily placed over a person's teeth without any external support structure. At the same time, the tray is sufficiently flexible that it can approximately conform to the person's teeth without any prior heating of the tray or formal customization. At ambient temperatures the tray is sufficiently thin and flexible so as to be comfortable-fitting.

In one embodiment, the pre-shaped dental tray is preloaded with a dental treatment composition, e.g., bleaching gel, making treatment simpler and easier compared to existing dental treatment regimens. Because of its simplicity and ease of use the tray may be sold over-the-counter for people wanting to whiten their own teeth, without the need for visits to a dental practitioner, resulting in a significantly less expensive alternative with good results.

The tray is preferably available in different configurations for treatment of the upper and lower dental arches. The tray includes at least two walls. According to one preferred embodiment, the tray includes a front side wall, a rear side wall, and a bottom wall. The tray is shaped to cover at least a portion of the rear surfaces of the teeth, the incisal edges, and especially the front surface of the teeth, which is the surface that is most often seen (and therefore most desirable to whiten). The trays may be configured to cover any desired number of teeth. In one embodiment, the trays may be sized and configured to cover at least 8 of the front upper teeth and at least 8 of the front lower teeth, depending on the size of the tray, especially the tray's side walls, which provide treatment to the front and back surfaces of the teeth. One advantage of using the pre-shaped dental trays according to the invention compared to bleaching strips is that the inventive dental trays according to the invention are better able to provide a dental treatment composition that is able to flow into the spaces between the teeth. In this way, the margins between the teeth can be better treated, e.g., bleached, compared to bleaching strips, which only reliably treat the front tooth surfaces and only if they are able to remain in place and not become prematurely dislodged.

Figure 1A:
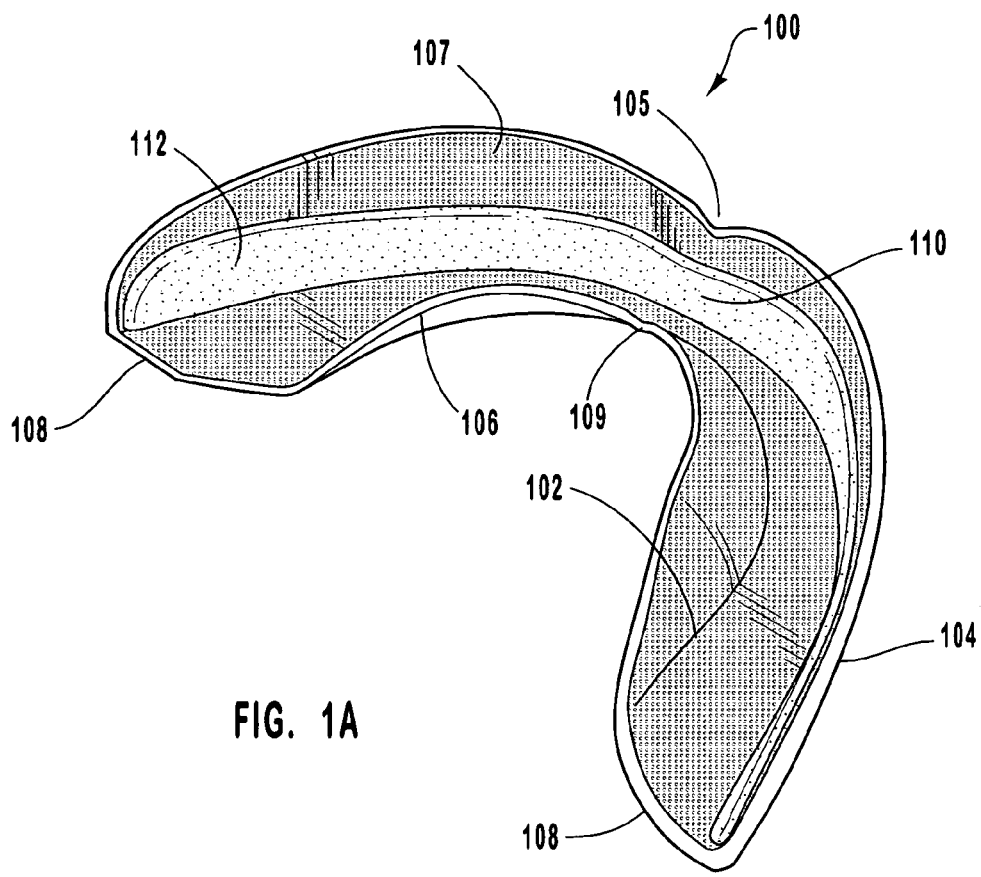
FIG. 1A is a perspective view of an exemplary embodiment of a pre-shaped, non-custom dental tray having a textured interior surface that is loaded with a dental treatment composition and configured for placement over the upper dental arch.

Referring now to the drawings, FIG. 1A illustrates an embodiment of a pre-shaped, non-custom dental tray 100 configured for placement over a person's upper dental arch. The dental tray 100 comprises a bottom wall 102 having a generally horseshoe-shaped configuration generally conforming to the size and shape of the person's upper dental arch. The bottom wall 102 of the illustrated embodiment has a generally flat profile, although it could have other shapes, as desired (e.g., curved). The dental tray 100 further includes a front side wall 104 extending laterally from a front end of the bottom wall 102 and a rear side wall 106 extending laterally from a rear end of the bottom wall 102. Together, the bottom wall 102, front side wall 104, and rear side wall 106 form a tray 100 that includes a hollow interior portion, or trough, that is open at the top, and that terminates at open ends 108.

The front side wall 104 of the tray 100 may extend substantially perpendicularly relative to the bottom wall 102, particularly at the ends 108 of the tray, although it may extend at any desired angle so as to conform or correspond to a person's teeth in a desired manner. The front side wall 104 of the tray 100 is generally taller toward the middle where it corresponds to the middle teeth and generally shorter toward the ends 108. Thus, the front side wall 104 tapers from front to back in order to approximately correspond to the descending height of teeth from the middle of the dental arch (i.e., at the incisors) toward the rear of the dental arch (i.e., at the molars).

In one embodiment, the front side wall 104 may include a notch 105. The notch 105 allows the tray to more easily spread open and conform to larger dental arches compared to dental trays that do no include this notch. In this way, the pre-shaped dental trays according to the invention can comfortably and effectively fit a larger range of varyingly-sized dental arches. The notch 105 is preferably formed near the middle portion 110, preferably at the top or edge of front side wall 104. The rear side wall 106 may also include a notch 109 that is able to substantially perform the same function as notch 105.

In addition, front side wall 104 may be textured so as to include a plurality of indentations formed in the inside surface of walls 102, 104, and 106. The plurality of indentations 107 may comprise a taffeta texture, tiny dimples, or a diamond grid texture, for example. In the embodiment illustrated in FIG. 1A, tray 100 includes a dense dimple texture evenly distributed over the entire inside surface of walls 102, 104, and 106 so as to provide multiple indentations adjacent to each tooth. Including indentations 107 provides tiny reservoirs that are able to hold additional quantities of a dental treatment composition, e.g., a bleaching gel, against the surfaces of a person's teeth and/or gums. Indentations 107 can be incorporated in any/all of the walls, as desired.

Like the front side wall 104, the rear side wall 106 of the tray 100 may be shorter and substantially perpendicular to the bottom wall 102 at the ends 108 of the horseshoe-shaped tray 100, but gradually open up to form a more oblique angle near a middle curved portion 110 of the tray so as to better accommodate the roof of the mouth near the middle portion 110 of the tray 100. The height of the rear side wall 106 is generally shorter than the corresponding section of the front side wall 104, particularly near the middle portion 110. This difference in height is to accommodate the differing height of the front versus the rear surface of the teeth in addition to the lower roof of the mouth relative to the rear side wall 106.

The bottom wall 102 has a width near the curved middle portion 110 of the tray that is advantageously less than the width of the bottom wall 102 between the middle portion 110 and the ends 108 of the tray 100. This allows for differences in the radial width of a person's incisors and canines relative to the much wider bicuspids and molars.

In one embodiment, the upper edges of front side wall 104 and rear side wall 106 are thickened and rounded. Rounding the edges of the tray provides greater comfort for the wearer. Thickening the edges helps the tray maintain structural integrity.

The pre-shaped dental tray 100 can be used to hold and maintain a dental treatment composition against a person's teeth. FIG. 1A depicts a bead 112 of a dental treatment composition that has been placed within the hollow interior portion, or trough, of the tray 100 adjacent to the front wall 104 and bottom wall 102 of the tray 100. When placed over a person's teeth, the bead 112 of the dental treatment composition will advantageously spread over the front surfaces of the person's teeth, and within the spaces between the teeth.

According to one embodiment (illustrated in FIG. 1A), the bead 112 is placed within the hollow interior, or trough, of the tray 100 adjacent to both the bottom wall 102 and the front wall 104. Bead 112 may be placed and sized so as to rise about two-thirds of the height of front wall 104. The dental treatment composition that forms bead 112 may form a dry skin over the composition, which aids in handling the tray 100 and bead 112.

Figure 1B:
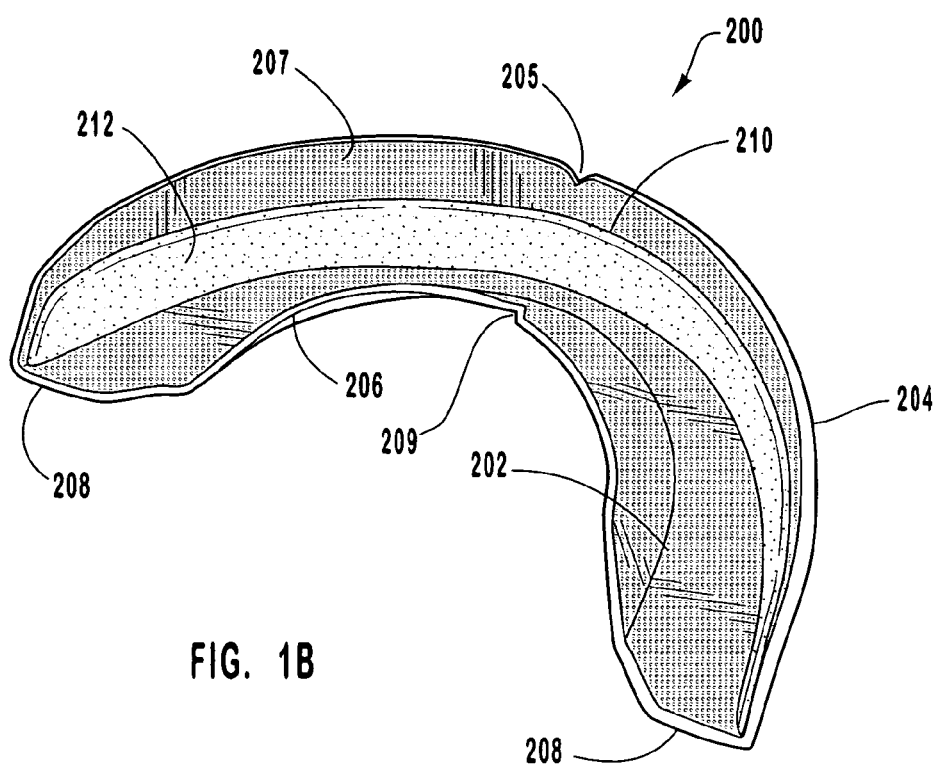
FIG. 1B is a perspective view of an exemplary embodiment of a pre-shaped, non-custom dental tray having a textured interior surface that is loaded with a dental treatment composition and configured for placement over the lower dental arch.

FIG. 1B illustrates an embodiment of a pre-shaped dental tray 200 configured for placement over a person's lower dental arch. The dental tray 200 comprises a bottom wall having a generally horseshoe-shaped configuration generally conforming to the shape of the person's lower dental arch. The bottom wall 202 has a generally flat planar profile, although it could have other shapes if desired (e.g., curved). The dental tray 200 further includes a front side wall 204 extending laterally from a front end of the bottom wall 202 and a rear side wall 206 extending laterally from a rear end of the bottom wall 202. Together, the bottom wall 202, front side wall 204, and rear side wall 206 form a tray 200 that includes a hollow interior portion, or trough, that is open at the top, and that terminates at open ends 208.

The front side wall 204 of the tray 200 may extend substantially perpendicularly relative to the bottom wall 202, particularly at the ends 208 of the tray, although it may extend at any desired angle so as to conform or correspond to a person's teeth in a desired manner. The front side wall 204 of the tray, 200 is generally taller toward the middle where it corresponds to the middle teeth and generally shorter toward the ends 208. Thus, the front side wall 204 tapers from front to, back; in order to approximately correspond to the descending height of teeth from the middle of the dental arch (i.e., at the incisors) toward the rear of the dental arch (i.e., at the molars).

Front side wall 204 may also include a notch 205 and rear side wall 206 may include a notch 209. The notches 205 and 209 function similar to notches 105 and 109, respectively, allowing the tray to spread open and more easily conform to larger-sized dental arches so as to comfortably fit over any of a range-of variously sized dental arches. Notches 205 and 209 are preferably formed near the middle portion 210, preferably at the top of front side wall 204 and rear side wall 206, respectively.

Figure 2A:
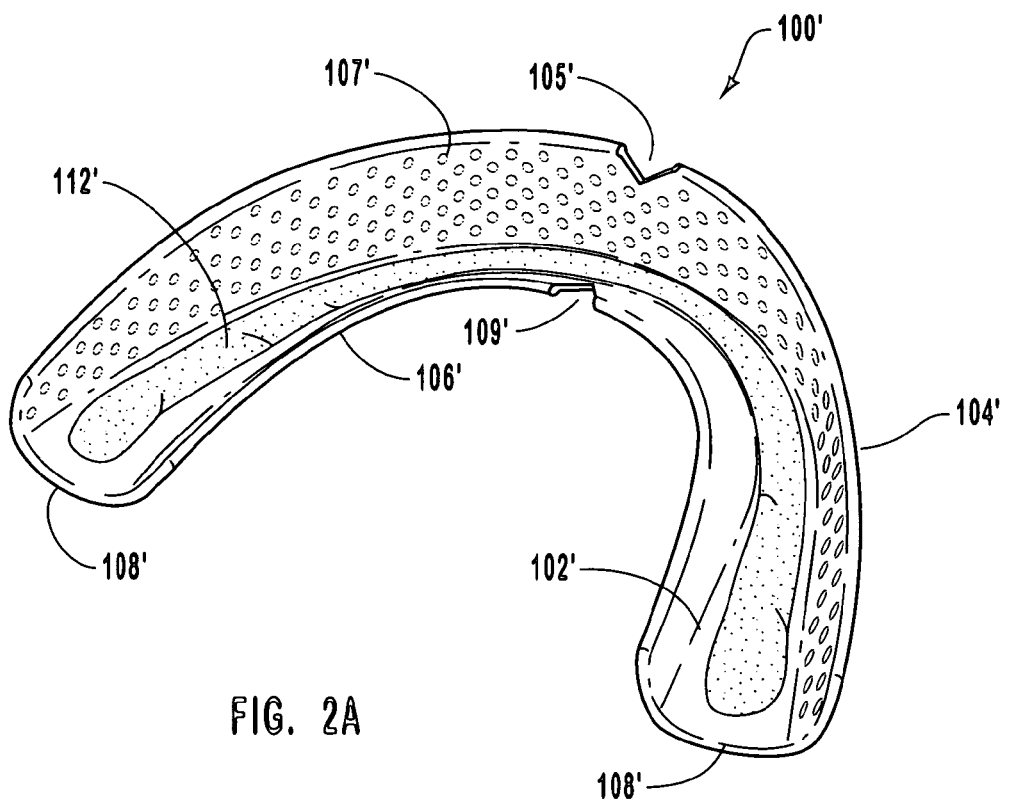
FIG. 2A is a perspective view of an alternative embodiment of a pre-shaped, non-custom dental tray having a dimpled interior surface that is loaded with a dental treatment composition and configured for placement over the upper dental arch.
Figure 2B:
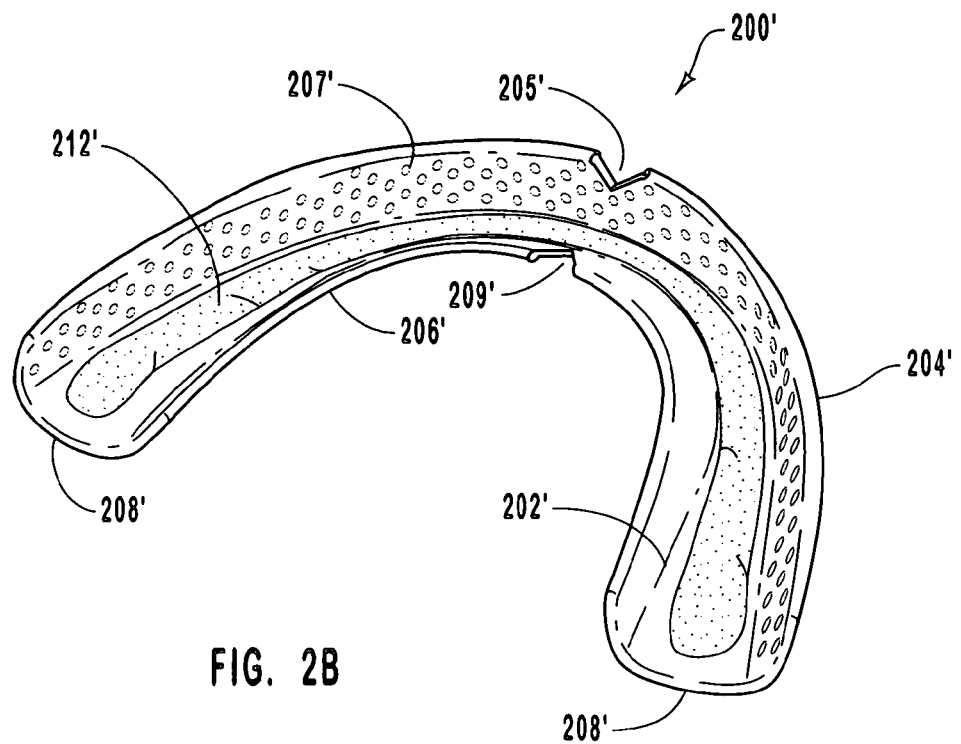
FIG. 2B is a perspective view of an alternative embodiment of a pre-shaped, non-custom dental tray having a dimpled interior surface that is loaded with a dental treatment composition and configured for placement over the lower dental arch.

The walls may be textured so as to include a plurality of indentations 207 formed in the inside surface of front side wall 204, rear side wall 206, and bottom wall 202. As shown in FIGS. 2A and 2B, indentations 207 are evenly distributed over the entire inside surface of front side wall 204 so as to provide multiple indentations adjacent to each tooth. Including indentations 207 provides tiny reservoirs that are able to hold additional quantities of a dental treatment composition, e.g., a bleaching gel, against the front surfaces of a person's teeth.

Like the front side wall 204, the rear side wall 206 of the tray 200 is short and substantially perpendicular to the bottom wall 202 at the ends 208 of the horseshoe-shaped tray 200, but gradually opens up to form a more oblique angle near a middle curved portion 210 of the tray so as to better accommodate the floor of the mouth near the middle portion 210 of the tray 200. The upper edges of front side wall 204 and rear side wall 206 may be thickened and rounded. Rounding the edges of the tray provides greater comfort for the wearer. Thickening the edges helps the tray better maintain structural integrity. A bead 212 of a dental treatment composition, e.g., a bleaching gel, is shown in the hollow interior portion, or trough, of the tray 200, adjacent to front side wall 204.

The height of the rear side wall 206 may be somewhat shorter than the corresponding section of the front side wall 204. This difference in height is to accommodate the differing height of the front versus the rear surface of the teeth in addition to the floor of the mouth relative to the rear side wall 206. Both side walls 204 and 206 (especially front side wall 204) are shorter than corresponding side walls 104 and 106 because of the generally smaller size of the lower teeth versus the upper teeth. The bottom wall 202 has a width near the curved middle portion 210 of the tray that is advantageously less than the width of-the bottom wall 202 between the middle portion 210 and the ends 208 of the tray 200. This allows for the differences in the radial width of a person's incisors and canines relative to the bicuspids and molars.

FIG. 2A illustrates an alternative embodiment of a pre-shaped, non-custom dental tray 100' configured for placement over a person's upper dental arch. The dental tray 100' comprises a bottom wall 102' a front side wall 104', and a rear side wall 106'. Together, the bottom wall 102', front side wall 104', and rear side wall 106' form a tray 100' that includes a hollow interior portion, or trough, that is open at the top, and that terminates at open ends 108'. The tray may include notches 105' and 109'. The tray 100' is illustrated as having larger dimples 107' formed in the inside surface of front side wall 104'. In addition, the bead of dental treatment composition 112' lies in the hollow interior, or trough, of the tray 100', adjacent to bottom wall 102'.

FIG. 2B illustrates an embodiment of a pre-shaped dental tray 200' configured for placement over a person's lower dental arch. The dental tray 200 comprises a bottom wall 202', a front side wall 204', and a rear side wall 206'. Together, the bottom wall 202', front side wall 204', and rear side wall 206' form a tray 200' that includes a hollow interior portion, or trough, that is open at the top, and that terminates at open ends 208'. The tray 200' may include notches 205' and 209'. The tray 200' is illustrated as having larger dimples 207' formed in the inside surface of front side wall 204'. In addition, the bead of dental treatment composition 212' lies in the hollow interior portion, or trough, of the tray 200', adjacent to bottom wall 202'.

Figure 3:
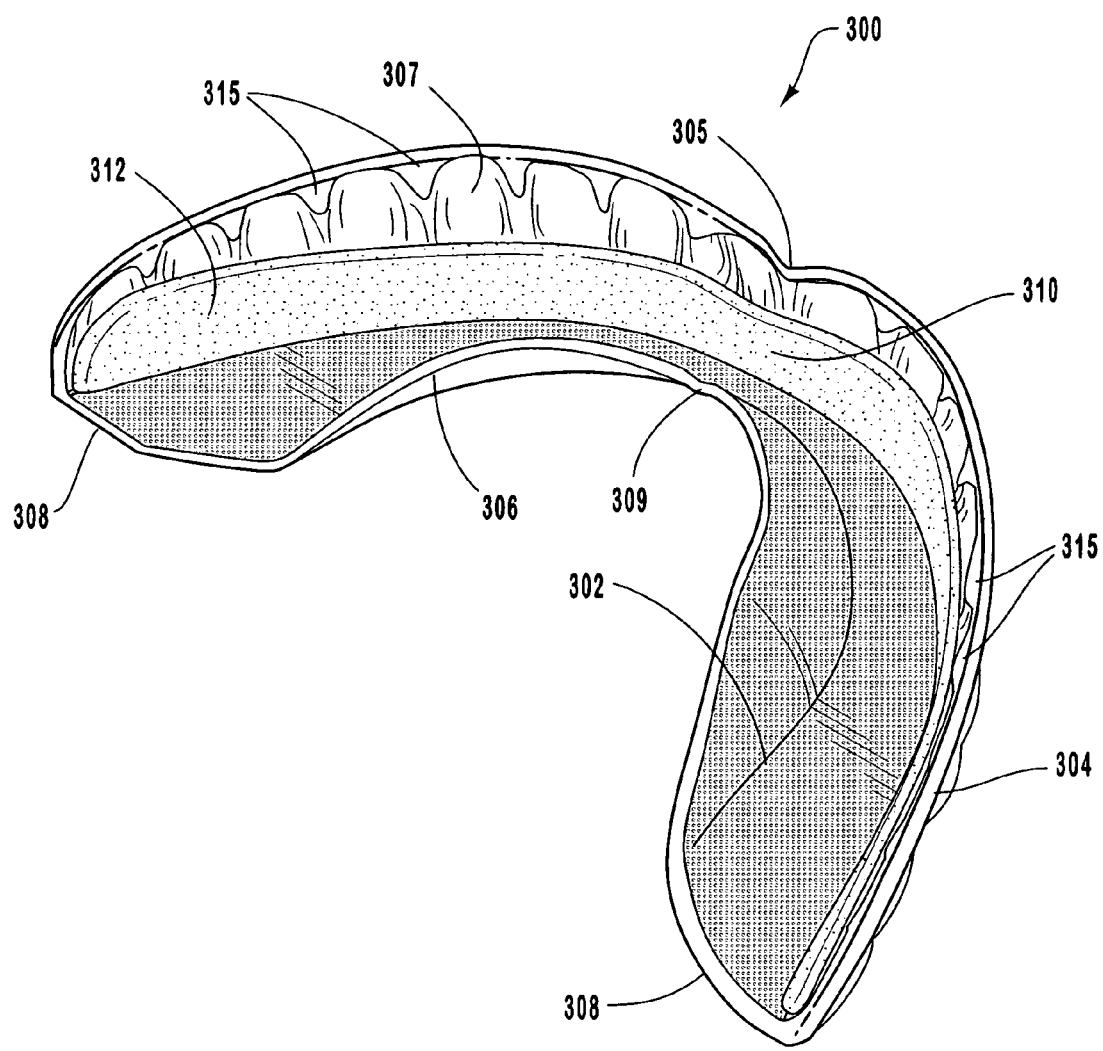
FIG. 3 depicts a preloaded dental tray according to the invention that is contoured to approximate the natural curvature of the labial and buccal surfaces of a person's teeth.

FIG. 3 depicts an exemplary pre-shaped dental tray 300 that is contoured so to as approximately correspond to the natural curvature of a person's teeth, particularly the labial and buccal surfaces of the teeth. As in the other trays depicted herein, the dental tray may include a bottom wall 302, a front side wall 304, and a rear side wall 306. Together, the bottom wall 302, front side wall 304, and rear side wall 306 form a tray 300 that includes a hollow interior portion, or trough, that is open at the top, and that terminates at open ends 308. The tray 300 may optionally include notches 305 and 309 near a middle portion 310. The tray 300 is illustrated as having a textured surface and a dental treatment composition 312. In addition, the tray 300 includes contours 307 that approximately correspond to the natural curvature of a person's teeth. The tray also optionally includes indentations 315 corresponding to the gingival between individual teeth.

Notwithstanding the foregoing, it should be understood that pre-shaped, non-customized dental trays within the scope of the invention can have any desired configuration such that the trays of FIGS. 1-3 are merely illustrative, non-limiting examples of pre-shaped dental trays configured for placement over the upper or lower dental arch.

The pre-shaped dental trays according to the invention can be made of any appropriate polymeric material that is able to provide a thin and flexible tray. Exemplary materials include low density polyethylene (LDPE) and ultra-low density polyethylene (LDPE or ULDPE). Alternative materials include ethylene-vinyl acetate copolymer (EVA) and polycaprolactone (PCL). Each material can be used alone or in combination with other polymers, such as polypropylene (PP), ethylene-vinyl acetate copolymer (EVA), polycaprolactone (PCL), and other forms of polyethylene (PE). Flow additives, fillers, plasticizers, and the like may be added as desired. LDPE, ULDPE, PE and PP are examples of polyolefins.

ULDPE refers to a range of-polyethylene-based copolymers defined as having a density of less than 0.914 g/cm3. LDPE is defined as having a density in a range of 0.915-0.94 g/cm3. For purposes of comparison, high density polyethylene (HDPE) is defined as having a density in a range of 0.94 to 0.97 g/cm3. Thus, LDPE and ULDPE can be readily distinguished from other forms of PE by density, although other physical properties may also differ in other respects, including water vapor transmission rate, crystallinity, melting point, coefficient of linear expansion, elasticity modulus, yield strength, tensile strength, hardness, and impact strength.

Any of various LDPE materials available from Dow Chemical may be used, as well as a number of ULDPE materials sold under the general trade name Attane® by Dow Chemical. In general, Attane® refers to polyethylene copolymers made from ethylene and octene. Specific examples include Attane® 4201 (density=0.912 g/cm3), Attane® 4202 (density=0.913 g/cm3), Attane® 4203 (density=0.905 g/cm3), Attane® 4301 (density=0.914 g/cm3), and Attane® 4404 (density=0.904 g/cm3). Another suitable ULDPE material is Exact® 4041 (density=0.878 g/cm3) made by Exxon-Mobil Chemical. An example of a suitable EVA material is Elvax® 250, available from DuPont. An example of a suitable PCL material is Capra® 650 from Solvoy-Interox. Other thermoplastic materials and blends used in making dental trays are disclosed in U.S. Pat. No. 5,769,633 to Jacobs et al., U.S. Pat. No. 5,051,476 to Uji et al., and U.S. Pat. No. 6,089,869 to Schwartz. For purposes of disclosing thermoplastic materials that can be made into dental trays, the foregoing patents are incorporated herein by reference.

According to one embodiment, the tray is formed of a mixture of EVA and PP, comprising about 5 percent to about 35 percent polypropylene (PP), more preferably about 10 percent to about 30 percent polypropylene (PP), and most preferably about 15 percent to about 25 percent polypropylene (PP). The balance comprises ethylene-vinyl acetate (EVA), and optionally small quantities of additives.

In one embodiment, the pre-shaped tray is formed by injection molding, although other manufacturing methods could be used. When forming the tray by injection molding, the thinness of the tray is limited by the degree to which the tray material can be successfully injection molded. Another method for forming the inventive trays is thermal assisted vacuum forming in which a preformed sheet of polymeric material is vacuum formed over a template corresponding to the size and shape of the finished dental tray. A punch die can be used to cut the finished tray from the excess sheet material.

In order for the inventive dental trays to have a desired level of flexibility, while also maintaining their ability to maintain their shape as a tray prior to use, the at least two walls (e.g. bottom walls, front side walls, and rear side walls) preferably have a thickness in a range of about 0.05 mm to about 1 mm, more preferably in a range of about 0.075 mm to about 0.75 mm, and most preferably in a range of about 0.1 mm to about 0.5 mm. The flexibility of the inventive dental trays allows them to at least partially conform to the person's teeth during use in order to approximate the comfort and fit of a custom dental tray without the need to formally customize the tray. Moreover, because the trays are not customized, the at least two side walls are substantially devoid of structures corresponding to the size and shape of a person's unique dentition so that the dental tray is designed to fit over a plurality of differently-sized dental arches corresponding to different people.

The dental trays according to the invention are useful for dental bleaching or to provide other desired dental treatments (e.g., one or more of antimicrobial, anticariogenic, remineralizing, and the like in addition to, or instead of, dental bleaching). In use, the dental tray is either provided preloaded with a bleaching or other dental composition, or a desired dental treatment composition is loaded into the dental tray by the user. The dental tray is then placed over the person's teeth to carry out a desired treatment regimen. The tray, coupled with the viscosity and stickiness of the dental treatment composition, work together to hold and maintain the treatment composition against the person's teeth. The non-customized dental trays according to the invention can be used once or repeatedly as desired.

Bleaching compositions used in combination with the dental treatment trays according to the present may advantageously be formulated so as to allow for substantially reduced treatment times as compared to typical home bleaching compositions, which are generally maintained in contact with the person's teeth for up to 8 hours or more (e.g., overnight while the user is sleeping). In contrast, bleaching compositions can be formulated so as to be more potent so that they can provide effective whitening in 30-60 minutes, preferably when applied in 5-7 consecutive daily treatments of 30-60 minutes each.

In one embodiment, the bleaching composition includes a bleaching agent, such as carbamide peroxide or hydrogen peroxide, or similar agents in concentrations substantially above those commonly used for over-the-counter teeth whiteners. Subjecting the teeth to higher concentrations of bleaching agent for a shorter period of time may, in some cases, cause less sensitivity in the teeth and less damage to adjacent tissues. By using higher concentrations of bleaching agent, the time period required to whiten teeth to a satisfactory level is greatly reduced.

When applying the bleaching gel compositions set forth herein it has been found that a desired amount of whitening can be achieved by five consecutive daily applications of no more than about 1 hour, while simultaneously having almost no sensitivity. Because of the short treatment time and lack of tooth sensitivity, the likelihood that users of the composition will complete the treatment is increased, increasing the probability of each user obtaining a desired degree of whitening.

A bleaching gel composition according to one embodiment includes, by weight: 16%-40% carbamide peroxide or 10%-20% hydrogen peroxide, 5-40% glycerin, 5-40% water, 10-60% polyethylene glycol (PEG) or polypropylene glycol (PPG) as thickening agents, 0-5% flavor, and 0-5% sweetener. Instead of, or in addition to PEG and PPG, the dental bleaching gel may include one or more of PVP, carboxypolymethylene, carboxymethyl cellulose, other cellulose gums, fumed silica, and the like, as tackifying agents useful in yielding a bleaching composition that is highly viscous and sticky. The treatment compositions may also include other active agents in addition to, or instead of, the dental bleaching agent, such as one or more desensitizing agents, anti-microbial agents, anti-tartar agents, anti-plaque agents, and remineralizing agents known in the art. The treatment compositions may include EDTA as a stabilizing agent and/or sodium phosphate and phosphoric acid as buffers.

Figure 4:
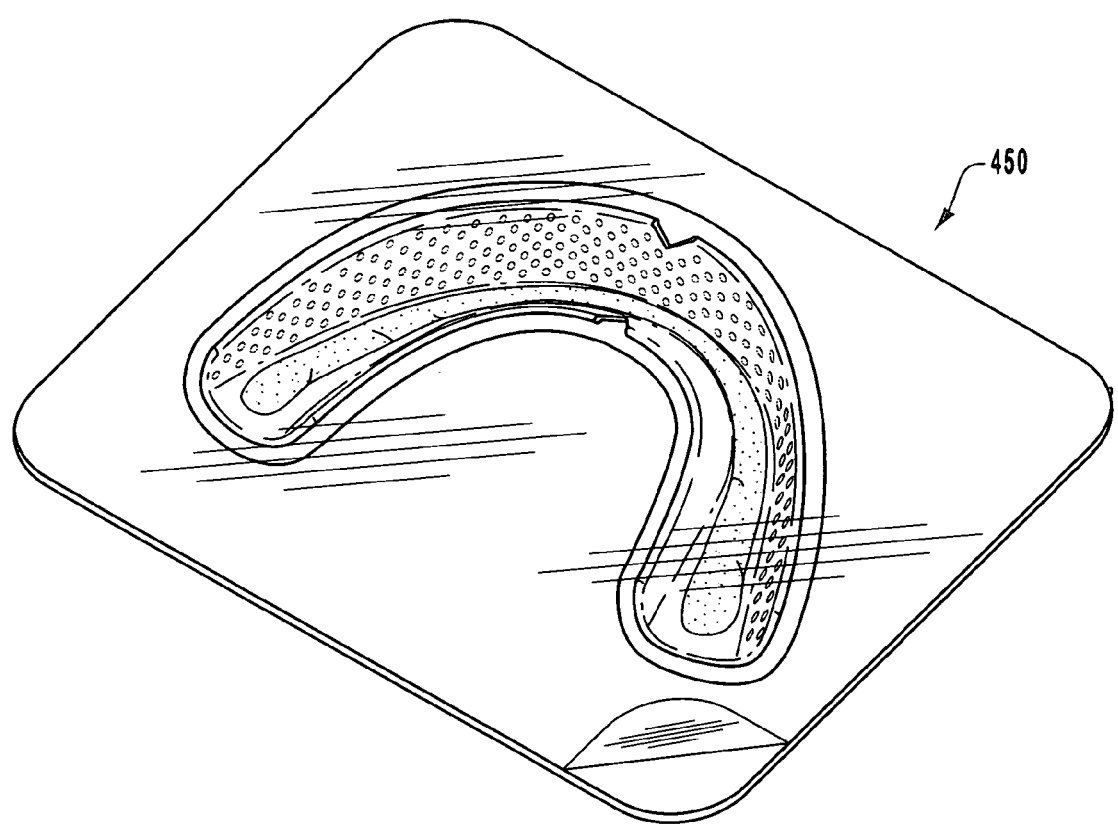
FIG. 4 depicts a preloaded dental tray according to the invention that is contained within a sealed packaging container.

In the case where a dental treatment tray according to the invention is pre-loaded with a dental bleaching composition having a relatively high concentration of a dental bleaching agent, or any other treatment compositions that may be less stable if exposed to air over time, it may be desirable for such pre-loaded dental treatments to be stored within a sealed packaging container prior to use. In this way, the treatment composition can be shielded from excessive air, and the composition and tray can be kept clean for sanitary reasons prior to use. An example of a sealed packaging container is depicted in FIG. 4, which depicts a pre-loaded dental treatment tray according to the invention sealed within a plastic packet 450. The packet can be torn open and the pre-loaded tray removed just prior to use. In the alternative, the dental bleaching or other treatment compositions may be provided in a separate container (e.g., a squeeze tube, not shown) and loaded into the dental tray by the user just prior to use.

FIG. 5 illustrates a preformed tray 100 (such as that illustrated in FIGS. 1A, 2A or 3) being placed by the user 514 over his or her upper dental arch. The tray is filled with a bleaching gel or other treatment composition 112 (as seen in FIGS. 1A, 2A or 3), which was either preloaded in the tray or placed in the tray just prior to use. The user 314 is easily able to place the non-customized tray over the upper dental arch without heating the tray in order to conform it to the teeth, and there are no external or internal supports needed to support the tray prior to use. The elimination of these steps is a significant advantage over other alternative trays because it makes use of the tray very simple and easy. With more complicated alternatives, problems occur during the heating and formation of the tray, which is a complex process, requiring the aid of a skilled dental practitioner to perform the customization of the tray correctly. The simplicity of the pre-formed non-customized tray of the present invention allows a user wanting to whiten his or her teeth to purchase the tray over the counter and perform the whitening treatment without the aid of a dental practitioner, resulting in a much less expensive tooth whitening regimen.

FIG. 6 illustrates a tray 200 such as that illustrated in FIGS. 1B, 2B or 3 being placed by the user 514 over his or her lower dental arch, optionally with the tray 100 as seen in FIG. 5 in place over the upper dental arch. The tray is filled with a bleaching gel or other treatment composition (as seen in FIGS. 1B, 2B and 3), which was either preloaded in the tray or placed in the tray just prior to use. The user 514 is easily able to place the pre-formed tray 200 over the lower dental arch, even while the tray 100 is in position over the upper dental arch. This is a further advantage of the invention, as it allows the person to treat both dental arches simultaneously, at low cost and with little effort.

The trays of the present invention may be provided as part of a dental bleaching kit containing one or more trays for upper and lower dental arches, and a bleaching gel and/or one or more other treatment compositions. Providing such a kit over-the-counter provides a relatively inexpensive alternative to people wanting to whiten their own teeth compared to more expensive at-home bleaching regimens that require the formation of a customized dental tray (e.g., boil-and-bite or trays formed using a stone model of the person's teeth).

The dental bleaching or other treatment composition is preferably sufficiently thick and sticky so as to hold the dental treatment tray against the user's teeth, and also to cause the tray to at least partially conform to the user's teeth. In this way, the non-custom dental trays according to the invention can be used to treat a wide variety of differently sized dental arches and teeth among different users without having to form a customized dental tray, as is commonly done for home bleaching regimens. By conforming to a particular user's teeth, the dental trays according to the invention at least partially emulate a customized tray in terms of comfort and efficacy in holding the dental treatment composition against the user's teeth.

The following are several examples of suitable bleaching compositions. Such exemplary compositions are given by way of example, and not by limitation, in order to illustrate dental bleaching compositions that have been found to be useful when used to bleach a person's teeth using the inventive dental treatment trays according to the invention. Unless otherwise indicated all percentages are by weight.

EXAMPLE 1

A dental bleaching composition suitable for use in combination with the dental trays disclosed herein was formed by mixing together the following components:

| | |
|---|---|
| Carbamide Peroxide | 31% |
| Glycerin (USP Kosher) | 8% |
| Water | 8% |
| Polyethylene Glycol 20,000 | 49% |
| Peach Flavor | 2% |
| Sodium Saccharin | 2% |

The resulting bleaching gel was easy to apply to the tray, was of moderate viscosity and was not so sticky that it could not be easily removed after the bleaching treatment by rinsing the user's mouth with water. Additionally, the composition had a pleasant taste and showed positive bleaching effects in a very short amount of time. Marked improvements in tooth coloration occurred within five days. Use of the composition also did result in noticeable tooth sensitivity such as that commonly associated with other at-home bleaching compositions that utilize carbamide peroxide even though the composition had approximately three times the amount of carbamide peroxide found in conventional at-home whitening kits.

EXAMPLE 2

A dental bleaching composition suitable for use in combination with the dental trays disclosed herein was formed by mixing together the following components:

| | |
|---|---|
| Carbamide Peroxide | 26% |
| Glycerin (USP Kosher) | 12% |
| Water | 6%, |
| Polyethylene Glycol 20,000 | 55% |
| Sodium Saccharin | 1% |

While the bleaching gel composition in Example 2 whitens teeth well, it did not taste as well as the dental bleaching composition made according to Example 1.

EXAMPLE 3

A dental bleaching composition suitable for use in combination with the dental trays disclosed herein was formed by mixing together the following components:

| | |
|---|---|
| Carboxymethylcellulose (Na+ salt) | 2% |
| Carbamide Peroxide | 22.5% |
| Glycerin (USP Kosher) | 28% |
| Water | 16.4% |
| Sodium Saccharin (powder) | 2% |
| Sodium EDTA | 0.1% |
| Cabosil M-5 (fumed silica) | 7% |
| Peach Flavor | 2% |
| Polyethylene Glycol 20,000 | 20% |

The resulting bleaching gel was easy to apply to the tray, was of moderate viscosity and was not so sticky that it could not be easily removed after the bleaching treatment by rinsing the user's mouth with water. Additionally, the composition had a pleasant taste and showed positive bleaching effects in a very short amount of time. Marked improvements in tooth coloration occurred within five days. Use of the composition also did result in noticeable tooth sensitivity such as that commonly associated with other at-home bleaching compositions that utilize carbamide peroxide even though the composition had approximately three times the amount of carbamide peroxide found in conventional at-home whitening kits.

EXAMPLE 4

A dental bleaching composition suitable for use in combination with the dental trays disclosed herein was formed by mixing together the following components:

| | |
|---|---|
| Carbamide Peroxide | 35% |
| Glycerin (USP Kosher) | 7% |
| Water | 9% |
| Polyethylene Glycol 10,000 | 44% |
| wintergreen flavor | 2% |
| Sodium Saccharin | 3% |

EXAMPLE 5

A dental bleaching composition suitable for use in combination with the dental trays disclosed herein was formed by mixing together the following components:

| | |
|---|---|
| Hydrogen Peroxide | 12% |
| Glycerin (USP Kosher) | 18% |
| Water | 13% |
| Polyethylene Glycol 20,000 | 50% |
| Peach Flavor | 4% |
| Sodium Saccharin | 3% |

The resulting composition was easy to apply and provided positive bleaching effects in a relatively short time frame, as discussed above.

EXAMPLE 6

A dental bleaching composition suitable for use in combination with the dental trays disclosed herein was formed by mixing together the following components:

| | |
|---|---|
| Hydrogen Peroxide | 19% |
| Glycerin (USP Kosher) | 14% |
| Water | 8% |
| Polyethylene Glycol 20,000 | 56% |
| Sodium Saccharin | 3% |

EXAMPLE 7

A dental bleaching composition suitable for use in combination with the dental trays disclosed herein was formed by mixing together the following components:

| | |
|---|---|
| Hydrogen Peroxide | 18% |
| Glycerin (USP Kosher) | 10% |
| Water | 13% |
| Polyethylene Glycol 10,000 | 50% |
| Wintergreen Flavor | 5% |
| Sodium Saccharin | 4% |

For each application, the tray is either preloaded with the bleaching gel or filled just a prior to insertion into the user's mouth. Because of the high level of carbamide peroxide or hydrogen peroxide, the tray is preferably kept in the mouth for less than about one hour. By providing the correct balance of viscosity and stickiness of the composition, the vast majority (i.e., more than about 90%) of the composition can easily be removed from the user's teeth within an hour simply by effervescence and the saliva in the user's mouth. This is an improvement over many existing teeth whitening compositions which are used for eight to twelve hours and which include materials designed to keep the composition on the user's teeth for a prolonged period. The compositions adhere to the user's teeth for prolonged periods as intended, but must sometimes be removed by brushing.

EXAMPLE 8

A dental bleaching composition suitable for use in combination with the dental trays disclosed herein was formed by mixing together the following components:

| | |
|---|---|
| Carboxy Methyl Cellulose (sodium salt) | 2% |
| Carbamide Peroxide | 22.5% |
| Glycerin | 28% |
| Water | 16.4% |
| Sodium Saccharine Powder | 2% |
| Sodium EDTA | 0.1% |
| Cabosil M-5 ($SiO_2$) | 7% |
| Peach Flavor | 2% |
| Polyethylene Glycol (M.W. = 20,000) | 20% |

The resulting dental bleaching gel was placed within a flexible, thin-walled dental tray and then placed over a person's teeth. Because the bleaching gel was sticky and viscous it was able to adhere and retain the flexible, thin-walled dental tray reasonably well against the person's teeth for a desired period of time (e.g., 1 hour or more).

EXAMPLE 9

A dental bleaching composition suitable for use in combination with the dental trays disclosed herein was formed by mixing together the following components:

| | |
|---|---|
| Water | 19.2% |
| Edetate Disodium | 0.1% |
| Carbamide Peroxide | 18.5% |
| Xylitol C | 7% |
| Glycerin | 25.4% |
| CARBOPOL 974 | 5.3% |
| NaOH (50% in water) | 4.5% |
| Carboxy Methyl Cellulose | 4% |
| Kollidon 90F | 10% |
| Peach Flavor | 3% |
| Sucralose (25% in water) | 3% |

The resulting dental bleaching gel was extremely thick. The resulting dental bleaching gel was placed within a flexible, thin-walled dental tray and then placed over a person's teeth. Because the bleaching gel was sticky and viscous it was able to adhere and retain the flexible, thin-walled dental tray reasonably well against the person's teeth for a desired period of time (e.g., 1 hour or more).

EXAMPLE 10

A dental bleaching composition suitable for use in combination with the dental trays disclosed herein was formed by mixing together the following components:

| | |
|---|---|
| Water | 18% |
| Edetate Disodium | 0.1% |
| Carbamide Peroxide | 18.5% |
| Sucralose (25% in water) | 3% |
| Glycerin | 41.6% |
| CARBOPOL 974 | 5.3% |
| NaOH (50% in water) | 4.5% |
| Kollidon 90F | 2% |
| Carboxy Methyl Cellulose | 4% |
| Peach Flavor | 3% |

The resulting dental bleaching gel was placed within a flexible, thin-walled dental tray and then placed over a person's teeth. Because the bleaching gel was sticky and viscous it was able to adhere and retain the flexible, thin-walled dental tray reasonably well against the person's teeth for a desired period of time (e.g., 1 hour or more).

EXAMPLE 11

A dental bleaching composition suitable for use in combination with the dental trays disclosed herein was formed by mixing together the following components:

| | |
|---|---|
| Water | 18% |
| EDTA | 0.1% |
| Carbamide Peroxide | 22% |
| Sucralose (25% in water) | 2% |
| Glycerin | 37.1% |
| CARBOPOL 974 | 5.3% |
| NaOH (50% in water) | 4.5% |
| Kollidon 90F | 2% |
| Carboxy Methyl Cellulose | 5% |
| Peach Flavor | 4% |

The resulting dental bleaching gel was placed within a flexible, thin-walled dental tray and then placed over a person's teeth. Because the bleaching gel was sticky and viscous it was able to adhere and retain the flexible, thin-walled dental tray reasonably well against the person's teeth for a desired period of time (e.g., 1 hour or more).

EXAMPLE 12

A dental bleaching composition suitable for use in combination with the dental trays disclosed herein was formed by mixing together the following components:

| | |
|---|---|
| Water | 18% |
| EDTA | 0.1% |
| Carbamide Peroxide | 22% |
| Sucralose (25% in water) | 2% |
| Glycerin | 40.1% |
| CARBOPOL 974 | 5.3% |
| NaOH (50% in water) | 4.5% |
| Kollidon 90F | 2% |
| Carboxy Methyl Cellulose | 5% |
| Peppermint Oil | 1% |

The resulting dental bleaching gel was placed within a flexible, thin-walled dental tray and then placed over a person's teeth. Because the bleaching gel was sticky and viscous it was able to adhere and retain the flexible, thin-walled dental tray reasonably well against the person's teeth for a desired period of time (e.g. 1 hour or more).

The present invention may be embodied in other specific forms without departing from its spirit or essential characteristics. The described embodiments are to be considered in all respects only as illustrative and not restrictive. The scope of the invention is, therefore, indicated by the appended, claims rather than by the foregoing description. All changes which come within the meaning and range of equivalency of the claims are to be embraced within their scope.

What is claimed is:

1. A pre-shaped, non-custom dental tray suitable for placement over at least a portion of one of a person's upper or lower dental arches, wherein the dental tray comprises at least one type of polymeric material, the dental tray further comprising:

at least two walls defining a hollow interior portion therebetween, wherein an entire interior surface of at least one of the walls includes a plurality of spaced-apart indentations therein for holding a treatment composition against a person's teeth when the dental tray is in use, the spaced-apart indentations being substantially evenly distributed across the entire interior surface of the at least one of the walls and so as to provide multiple indentations adjacent to each tooth when the dental tray is in use, wherein the dental tray is substantially devoid of structures corresponding to the size and shape of a person's unique dentition so that the dental tray is designed to comfortably fit over a plurality of differently-sized dental arches corresponding to different people, wherein the dental tray has a maximum wall thickness of less than about 1 mm in order to be flexible across its entirety so that, when the non-custom dental tray is placed over a person's teeth, the entire tray can flex and thereby at least partially conform to the person's teeth during use in order to approximate the comfort and fit of a custom dental tray without the need to formally customize the tray.

2. A pre-shaped, non-custom dental tray as defined in claim 1, wherein the at least two walls include a front side wall, a rear side wall, and a bottom wall interconnecting the front and rear side walls, wherein the front side wall, rear side wall and bottom wall each have a substantially uniform wall thickness of less than about 1 mm.

3. A pre-shaped, non-custom dental tray as defined in claim 1, wherein the spaced-apart indentations comprise at least one of a taffeta texture, tiny dimples, or a diamond grid texture.

4. A pre-shaped, non-custom dental tray as defined in claim 1, wherein the dental tray is formed from a mixture comprising ethylene vinyl acetate (EVA) and polypropylene (PP).

5. A pre-shaped, non-custom dental tray as defined in claim 4, wherein the mixture comprises from about 10% to about 30% by weight PP, with the balance consisting essentially of EVA.

6. A pre-shaped, non-custom dental tray as defined in claim 4, wherein the mixture comprises from about 15% to about 25% by weight PP, with the balance consisting essentially of EVA.

7. A pre-shaped, non-custom dental tray as defined in claim 1, wherein the dental tray has a maximum thickness of less than about 0.75 mm.

8. A pre-shaped, non-custom dental tray as defined in claim 1, wherein the dental tray has a maximum thickness of less than about 0.5 mm.

9. A pre-shaped, non-custom dental tray as defined in claim 1, wherein the dental tray is sized and configured so as to approximately terminate at or near a person's gingival margin when the dental tray is placed over the person's teeth.

10. A pre-shaped, non-custom dental tray suitable for placement over at least a portion of one of a person's upper or lower dental arches, wherein the dental tray comprises at least one type of polymeric material, the dental tray further comprising:

at least two walls defining a hollow interior portion therebetween, wherein an entire interior surface of at least one of the walls includes a plurality of spaced-apart indentations formed therein and substantially evenly distributed over the entire interior surface of the at least two walls, the spaced-apart indentations being arranged so as to provide multiple indentations adjacent to each tooth when the dental tray is in use and so as to form at least one of a taffeta texture, evenly distributed tiny dimples, or a diamond grid texture for holding a treatment composition against a person's teeth when the dental tray is in use, wherein the dental tray is substantially devoid of structures corresponding to the size and shape of a person's unique dentition so that the dental tray is designed to comfortably fit over a plurality of differently-sized dental arches corresponding to different people, wherein the dental tray has a maximum wall thickness of less than about 1 mm in order to be flexible across its entirety so that, when the non-custom dental tray is placed over a person's teeth, the entire tray can at least partially conform to the person's teeth during use in order to approximate the comfort and fit of a custom dental tray without the need to formally customize the tray.

11. A method of treating a person's teeth, comprising:

providing a non-custom dental tray according to claims 1, or 10;

placing a dental treatment composition into the hollow interior portion of the dental tray; and positioning the dental tray over the person's teeth in order to contact the teeth with the treatment composition.

\* \* \* \* \*

UNITED STATES PATENT AND TRADEMARK OFFICE
CERTIFICATE OF CORRECTION

PATENT NO. : 7,481,653 B2
APPLICATION NO. : 11/054696
DATED : January 27, 2009
INVENTOR(S) : Andersen Page 1 of 1

It is certified that error appears in the above-identified patent and that said Letters Patent is hereby corrected as shown below:

Column 1
Line 26, after "either" delete "a"

Column 4
Line 28, change "kept" to --keep--

Column 6
Line 16, change "end:" to --end--
Line 17, change "-and" to --and--

Column 8
Line 49, change "200" to --200'--

Column 11
Line 38, change "314" to --514--

Column 14
Line 25, after "just" delete "a"

Signed and Sealed this

Twenty-ninth Day of September, 2009

David J. Kappos
*Director of the United States Patent and Trademark Office*